United States Patent [19]

Martin

[11] Patent Number: 5,395,316
[45] Date of Patent: Mar. 7, 1995

[54] TRIPLE LUMEN CATHETER

[75] Inventor: Geoffrey S. Martin, Mississauga, Canada

[73] Assignee: Med-Pro Design, Inc., Mississauga, Canada

[21] Appl. No.: 104,701

[22] Filed: Aug. 11, 1993

[51] Int. Cl.⁶ .............................................. A61M 3/00
[52] U.S. Cl. ..................................... 604/43; 604/280; 604/283; 604/284
[58] Field of Search ................. 604/43, 280, 283, 284, 604/905

[56] References Cited

U.S. PATENT DOCUMENTS

| | | | |
|---|---|---|---|
| 2,576,766 | 11/1951 | Sokolik | 128/240 |
| 4,072,146 | 2/1978 | Howes | 128/205 |
| 4,180,068 | 12/1979 | Jacobsen et al. | 128/214 |
| 4,717,379 | 1/1988 | Ekholmer | 604/43 |
| 4,894,057 | 1/1990 | Howes | 604/280 |
| 4,895,561 | 1/1990 | Mahurkar | 604/43 |
| 4,995,865 | 2/1991 | Gahara et al. | 604/43 |
| 5,135,599 | 8/1992 | Martin et al. | 156/294 |
| 5,207,228 | 5/1993 | Roelandt et al. | 128/713 |
| 5,215,527 | 6/1993 | Beck et al. | 604/43 |
| 5,292,305 | 3/1984 | Boudewijn et al. | 604/43 |

FOREIGN PATENT DOCUMENTS 0322225 6/1989 European Pat. Off. .... A61M 25/00

Primary Examiner—Jerome L. Kruter
Attorney, Agent, or Firm—Rogers & Scott

[57] ABSTRACT

The invention provides a catheter having a main body extending longitudinally between proximal and distal ends and including a tip structure at the distal end, a transition portion extending from the tip structure, and a shaft extending from the transition portion to the proximal end. The main body defines first, second and third lumens, the first and second lumens extending from the proximal end to the transition portion, and the third lumen extending from the proximal to the distal end. The side lumens are separated from the central lumen by parallel walls. In a preferred embodiment for use in dialysis, the side lumens are coupled to one another at the proximal end so that both side lumens receive intake blood and the treated blood is returned through the central lumen. Because the first and second lumens have intakes at different locations about the periphery of the main body, there is less likelihood that these lumens will be occluded by engagement with the wall of a blood vessel.

6 Claims, 5 Drawing Sheets

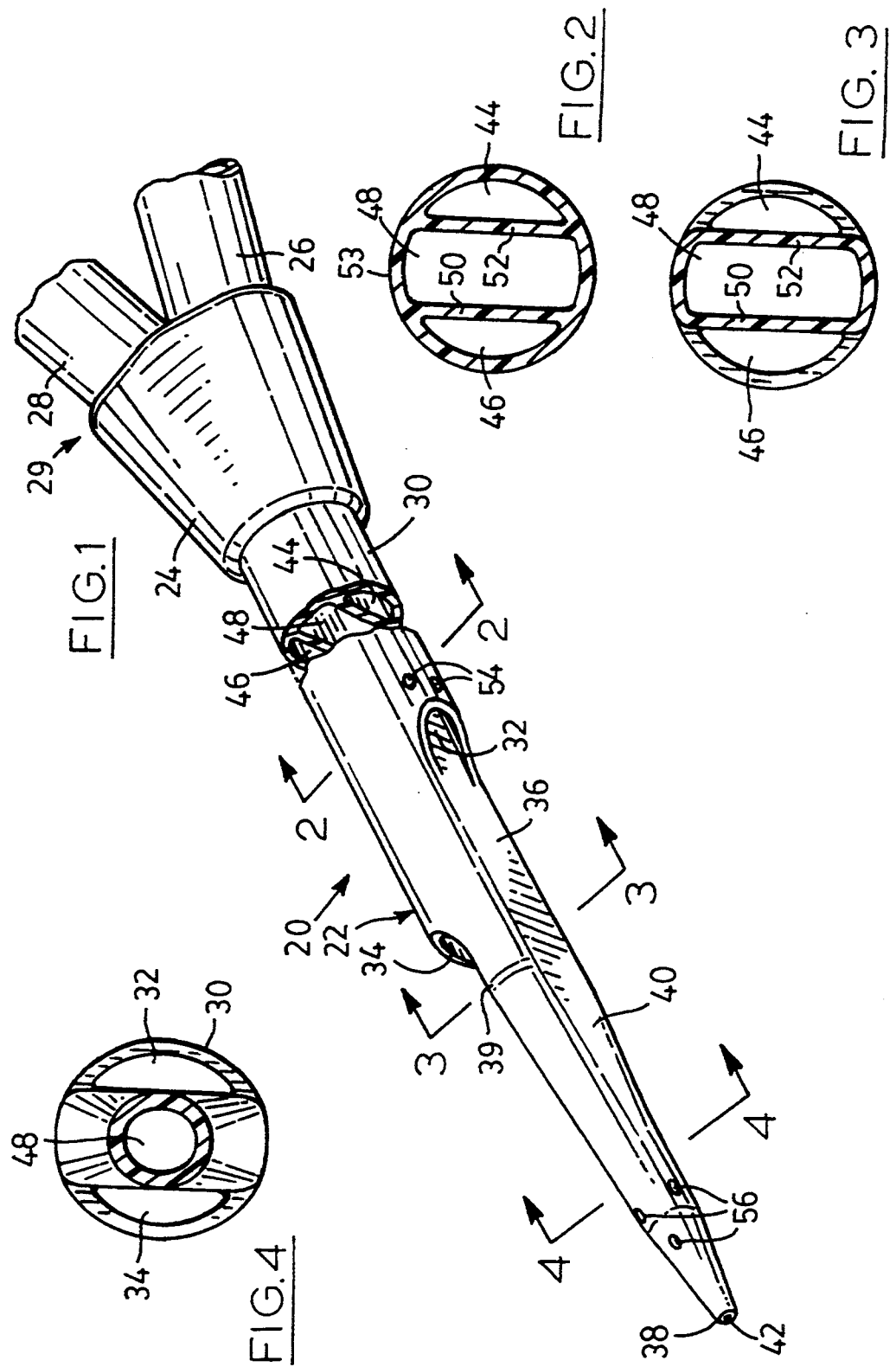

TRIPLE LUMEN CATHETER

BACKGROUND OF THE INVENTION

This invention relates to a dual flow catheter and more particularly for such a catheter for insertion into a blood vessel to facilitate haemodialysis treatments.

The invention will be described with particular reference to haemodialysis procedures, but it is envisaged that the invention could be put to other medical uses.

The procedure of haemodialysis requires that blood be removed for treatment through a catheter having an intake lumen, and that after treatment, the blood be returned through a return lumen either in a separate catheter or in the same catheter. It has become quite common to provide dual flow catheters which have two lumens arranged one to receive untreated blood and the other to return the treated blood to the patient. Such catheters fall into two distinct types namely "co-axial" catheters and "side-by-side" catheters. The co-axial catheters provide dual flows through a first lumen defined by a central tube and through a second lumen defined by an annular space between the central tube and an outer tube. By contrast the side-by-side catheters provide two similar lumens arranged in parallel one with the other. In both types of catheter one of the lumens is the intake lumen and receives blood from a first location, and the other lumen is the return lumen and returns the blood to a second location spaced downstream in the blood vessel from the first one to thereby minimize the risk of treated blood returning and reducing the efficiency of the dialysis treatment.

Co-axial catheters have some advantages over side-by-side catheters and vice-versa. For instance, in a co-axial catheter openings can be provided around the complete periphery for blood intake to minimize the risk that the catheter will be drawn against a blood vessel thereby occluding the intake openings. By contrast, in a side-by-side relationship, the openings can be provided on one side only and this side can become occluded by engagement with the wall. On the other hand, the side-by-side arrangement tends to have more resistance to kinking when it is bent than does the co-axial catheter.

SUMMARY OF THE INVENTION

The present invention is directed towards the side-by-side arrangement and is intended to overcome some of the disadvantages of that arrangement, including the problem of occlusion by engagement with the blood vessel wall.

Accordingly the invention provides a catheter having a main body extending longitudinally between proximal and distal ends and including a tip structure at the distal end, a transition portion extending from the tip structure, and a shaft extending from the transition portion to the proximal end. The main body defines first, second and third lumens, the first and second lumens extending from the proximal end to the transition portion, and the third lumen extending from the proximal to the distal end. The side lumens are separated from the central lumen by parallel walls. In a preferred embodiment especially useful for use in dialysis, the side lumens are coupled to one another at the proximal end so that both side lumens receive intake blood and the treated blood is returned through the central lumen. Because the first and second lumens have intakes at different locations about the periphery of the main body, there is less likelihood that these lumens will be occluded by engagement with the wall of a blood vessel.

BRIEF DESCRIPTION OF THE DRAWINGS

The invention will be better understood with reference to the following description taken in combination with the drawings, in which:

FIG. 1 is a diagrammatic isometric view of the main portions of a catheter according to a preferred embodiment of the invention especially useful in placement by surgical cut-down techniques;

FIG. 2 is a sectional view drawn to a larger scale on line 2—2 of FIG. 1;

FIG. 3 is a view similar to FIG. 2 and drawn on line 3—3 of FIG. 1;

FIG. 4 is a view similar to FIG. 2 and drawn on line 4—4 of FIG. 1;

DESCRIPTION OF THE PREFERRED EMBODIMENTS

Figure 5:
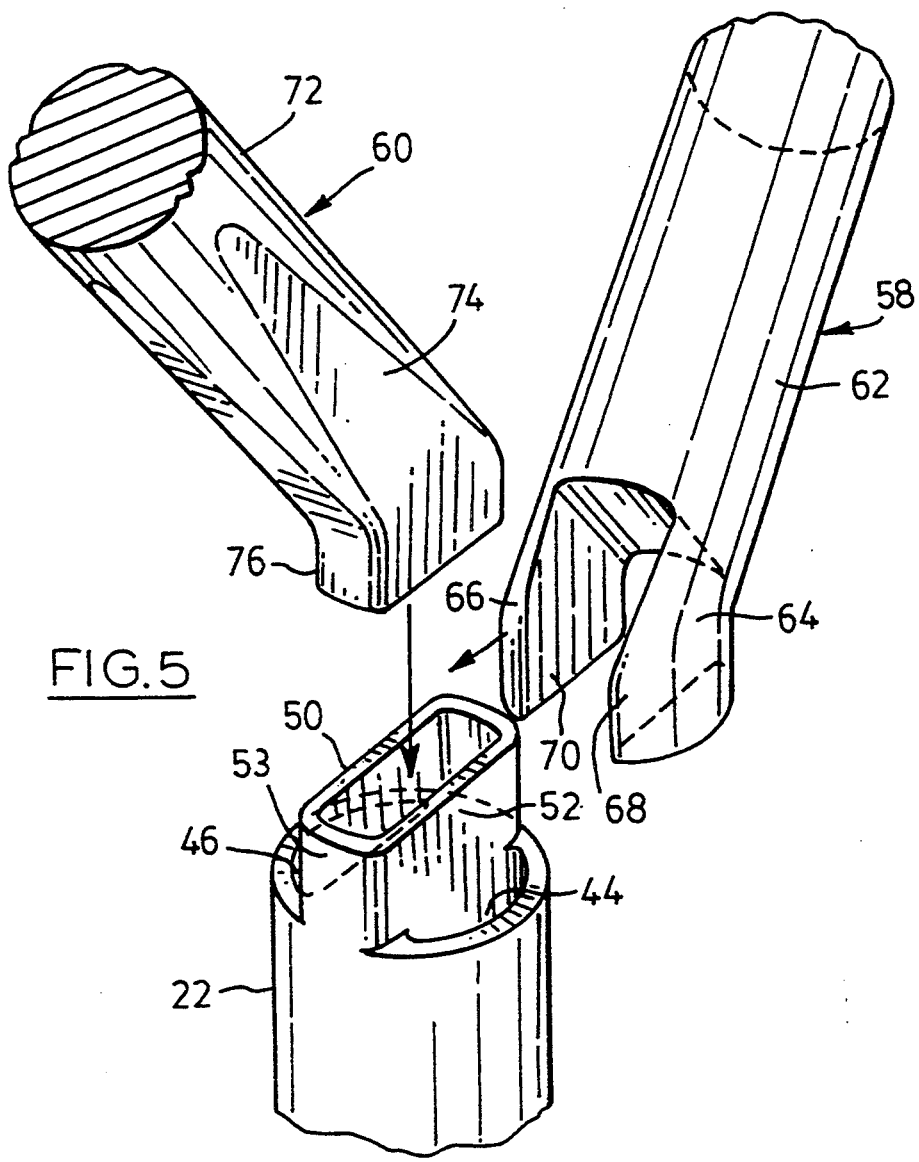
FIG. 5 is an exploded isometric view illustrating mandrels used in a preferred procedure for manufacturing the proximal end attachment structure of the catheter.

Reference is made firstly to FIG. 1 which illustrates a catheter indicated generally by the numeral 20 and consisting essentially of a main body 22 attached to a connector 24 which in turn receives respective intake and return tubes 26, 28 all of which form parts of a conventional attachment structure 29. When used for haemodialysis, which is exemplary for this invention, blood will be drawn from the patient through the tube 26 and returned through the tube 28.

The main body 22 extends longitudinally and has an elongate shaft 30 (which for clarity of drawing has been shortened by breaking the shaft) and the shaft ends at a transverse first intake opening 32. A transition portion 36 extends from the intake opening 32 to about the beginning of a change in section indicated by the lines 39. A second transverse intake opening 34 is located on the transition portion 36 and a tip structure 40 extends from lines 39 to the distal end of the main body 22 and a return opening 42 at the distal end.

As seen with reference to FIG. 2, the shaft 30 defines in cross-section three lumens 44, 46, and 48. First and second lumens 44, 46 are similar side lumens with the lumen 48 being a central lumen. The arrangement is preferably such that the lumens 44, 46 have similar cross-sections and the sum of the areas of these cross-sections is equal to the area of the lumen 48 to give similar intake and return flows as will be explained. The lumens are separated by a pair of parallel walls 50, 52 attached to a peripheral outer wall 53. This structure serves to increase the resistance to kinking when the body is bent.

As seen in FIGS. 1 and 2, the first lumen 44 terminates at its distal end at intake opening 32 which is defined by cutting part of the extrusion forming the shaft 30 to expose an end of the lumen 44. Similarly, lumen 46 terminates at end opening 34 which is spaced on the opposite side of the main body and longitudinally towards the distal end 38. The lumens 44, 46 also define side openings 54 (some of which can be seen) to improve the flow into the lumen and to minimize the pressure drop across the intake holes 32, 34.

As best seen in FIG. 3, the cross-section adjacent the lines 39 is similar to the cross-section shown at FIG. 2 with the exception that the side lumens 44, 46 have been cut away leaving the walls 50, 52 and the remaining portion of the outer wall 53 of the extrusion to define the central third lumen 48. Moving towards the distal end, it will be apparent by comparison of the cross-section shown in FIGS. 3 and 4 that the tip structure 40 is shaped to change from the line 39 defining the end of transition portion 36, and shown in section in FIG. 3, to a round cross-section which continues to define the lumen 48. Clearly this represents a reduction in cross-sectional area and the change is exaggerated in the drawings for the purposes of illustration. In practice, the cross-sectional area of the lumen 48 will remain substantially constant as it changes in shape and will then taper down to the opening 42. Pressure relief is provided by side holes 56 to minimize the possibility of flow restriction caused by the taper.

As will be explained, the intake tube 26 is connected for fluid continuity through the connector 24 with the first and second lumens 44, 46 at opposite sides of the main body 22. These lumens are in communication with one another as well as with the intake tube 26. However they are isolated from the fluid path formed in the connector 24 and extending between the third lumen 48 and the return tube 28. This will become evident with reference to FIG. 5.

The structure of the main body 22 is such that because there are two inlet openings 32, 34 spaced diametrically opposite one another about the body 22, there is little likelihood of occlusion of both of these openings simultaneously. Also, intake suction pressure will not build up at one of the openings to the same extent as it would when a single opening intake is used, and this also helps to resist the tendency for the catheter to be sucked towards a blood vessel wall with resulting occlusion of the intake. A further advantage is that the third lumen 48 is centrally located and proportioned to make it possible to use a Seldinger wire through this lumen and out through the suitably sized central return opening 42 at the distal end. However, if a Seldinger wire is to be used, it may be desirable to enter rods through tube 26 and into the lumens 44, 46 to temporarily occlude the openings 32, 34 to minimize the risk of tissue damage during tissue dilation as the catheter travels along the Seldinger wire. An alternative embodiment better suited to insertion over a wire will be described with reference to FIG. 8.

This catheter would also be placed in blood vessels using surgical cut-down techniques and this would obviate any need to use mandrels to close the lumens 44, 46 during insertion.

Figure 6:
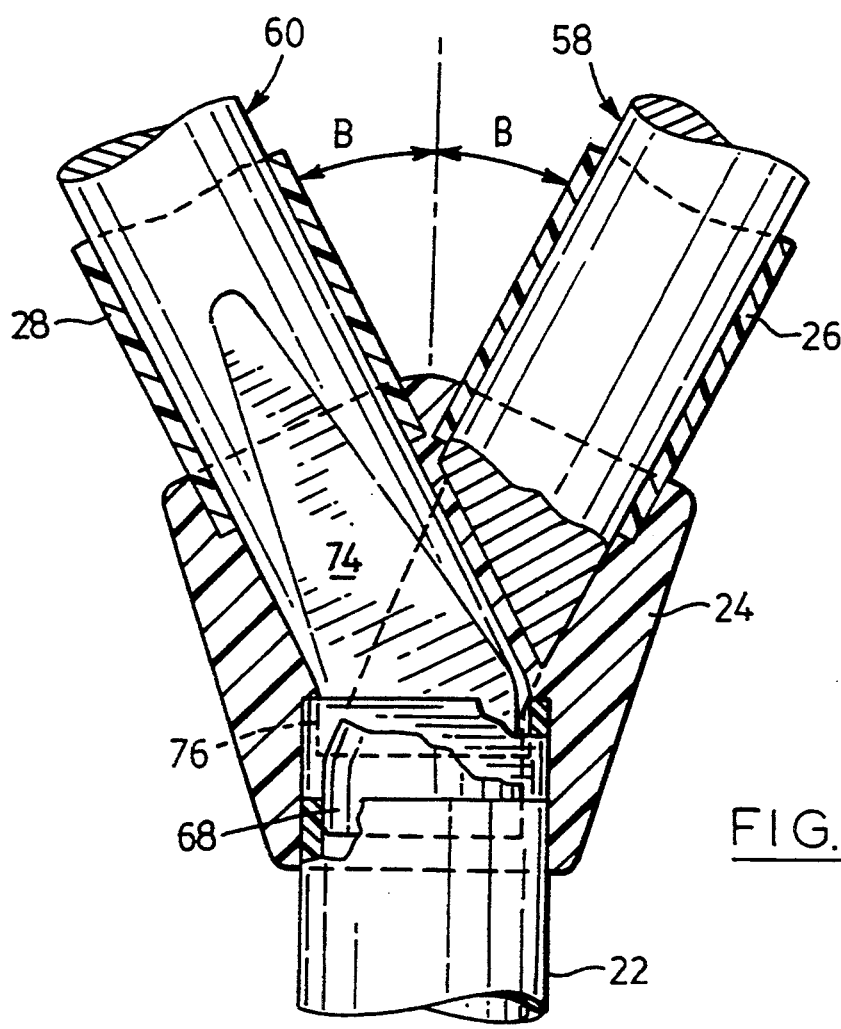
FIG. 6 is a sectional view of the proximal end attachment structure after completion and before removing the mandrels.

Reference is next made to FIG. 5 which illustrates diagrammatically a preferred method of making the connector 24. Reference will also be made to FIG. 6 which illustrates the finished connector in sectional view.

As seen in FIG. 5, the main body 22 is cut at its proximal end to expose the third or central lumen 48 defined by the parallel walls 50, 52 and part of the peripheral outer wall 53. The arrangement is such that respective first and second mandrels 58, 60 can be engaged in the proximal end of the main body 22 within a mold and then, using injection molding techniques, the material of the connector 24 can be injected around this assembly. To do this, the mandrel 58 is first engaged. This mandrel has a cylindrical main portion 62 terminating at bifurcate legs 64, 66 which initially form a continuation of the main portion and then have offset generally D-shaped end portions 68, 70 shaped and positioned relative to one another so that these end portions will slide into the respective first and second lumens 44, 46 with the walls 50, 52 engaged against the respective legs 64, 66. Next, the second mandrel 60 is engaged. This also has a cylindrical main portion 72 which leads through a tapered portion 74 to a generally rectangular and offset end portion 76 shaped to fit tightly within the third lumen 48.

The mandrels 58, 60 are assembled in the proximal end of the main portion 22 within the confines of a suitable mold shaped to define the external appearance of the connector 24 (FIG. 1) after injection molding. Tubes 26, 28 are engaged over the mandrels leaving parts of the mandrels exposed so that the mandrels can be pulled out of the completed assembly. With everything in place, injection molding takes place and the result can be seen in FIG. 6 where it will be evident that the clearance between the mandrels 58, 60 ensures that mold material separates the flow paths from one another and allows fluid continuity between the lumens 44, 46 and tube 26 independently of fluid continuity between the lumen 48 and the tube 28.

After molding and a suitable time for cooling, the mandrels can be simply pulled out of the assembly because the material has sufficient flexibility to permit this to take place. The result is a clean and well defined fluid communication between the lumens and the respective tubes.

As seen in FIG. 6, the assembly results in the tubes extending generally longitudinally and angled with respect to the longitudinal axis of the main body by an angle "B". This angle is preferably kept relatively small to keep the tubes more or less in line with the main body and is preferably about 15 degrees. Put another way, the tubes extend away from the main body spaced equally to either side of the axis of the main body and include an angle of about 30 degrees. It should also be noted that this angle can be reduced if required by using suitable mandrels and mold. However for practical purposes it will not normally be less than about 15 degrees.

Figure 7:
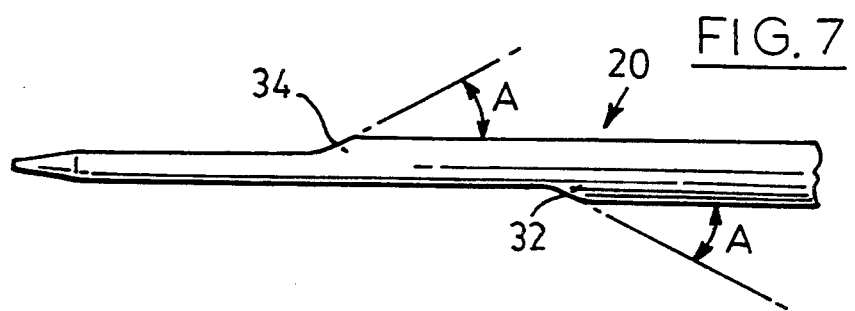
FIG. 7 is a diagrammatic view illustrating the geometrical relationships and the terminations of the lumens.

Reference is next made to FIG. 7 to describe a further advantageous feature of the catheter 20. In this diagrammatic representation, the openings 32, 34 are seen from the side and the angle these openings define with reference to the longitudinal extent of the catheter is indicated by the angle 37 A". While these angles need not necessarily be the same, they are preferably about 30 degrees in order to further minimize the risk of occlusion by a blood vessel wall. Clearly for the purposes of smooth engagement through body tissue (where a guide wire is used) this angle should be as small as possible whereas to minimize occlusion by the blood vessel in use, the angle should be nearer 90 degrees. It has been found that an angle in the order of 30 degrees provides sufficient lead-in when dilating tissue that the catheter can be engaged over a Seldinger wire and yet in use the wall of the blood vessel is unlikely to follow the contour of the catheter around the openings 32, 34.

Figure 8:
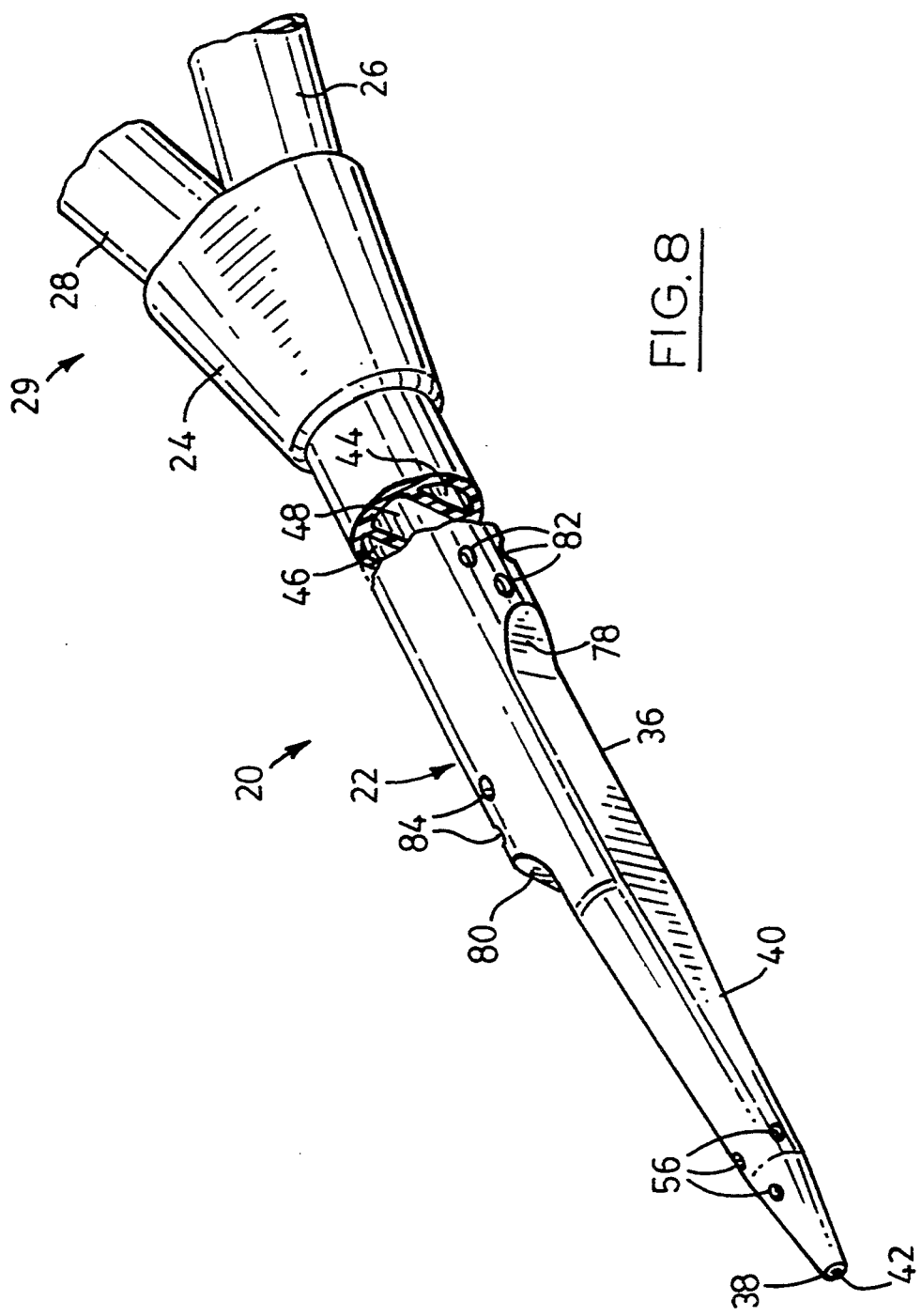
FIG. 8 is a view similar to FIG. 1 and showing the main portions of an alternative embodiment of the catheter especially useful for placement over a wire.

Reference is next made to FIG. 8 to illustrate an alternative embodiment of the invention. Similar parts are given the same numerals as those used with reference to similar parts of FIG. 1.

It will be seen that in this embodiment, the intake lumens 44, 46 terminate at blind ends defined by respective walls 78, 80 and access to these lumens is provided through side openings 82, 84 adjacent the blind ends rather then through the extreme ends of the lumens as is provided in FIG. 1. The catheter shown in FIG. 6 may be more acceptable to some practitioners for use in placing the catheter over a Seldinger wire because the walls 78, 80 will dilate tissue as the catheter is moved down the wire. Otherwise, the catheter shown in FIG. 8 is similar to that shown in FIG. 1.

The blind ends are preferably formed by a heating process which closes the side lumens at the transition portion to create the walls defining the blind ends. Such processes are common in the art because the materials used are thermoplastic.

Clearly it would be possible to have a catheter that is different from both the catheters shown in that one of the lumens 44, 46 could end in a wall and the other be open. It is also possible to change the positions of these openings and they could in fact be on directly opposite sides of the catheter without any longitudinal separation.

The preferred material for catheters according to this invention is polyurethane although the choice of material could change with use. When the catheter is to be fed over a guide wire the material is polyurethane having a 60 to 65D durometer whereas catheters placed by other techniques for longer term use would be 80-85A durometer.

Figure 9:
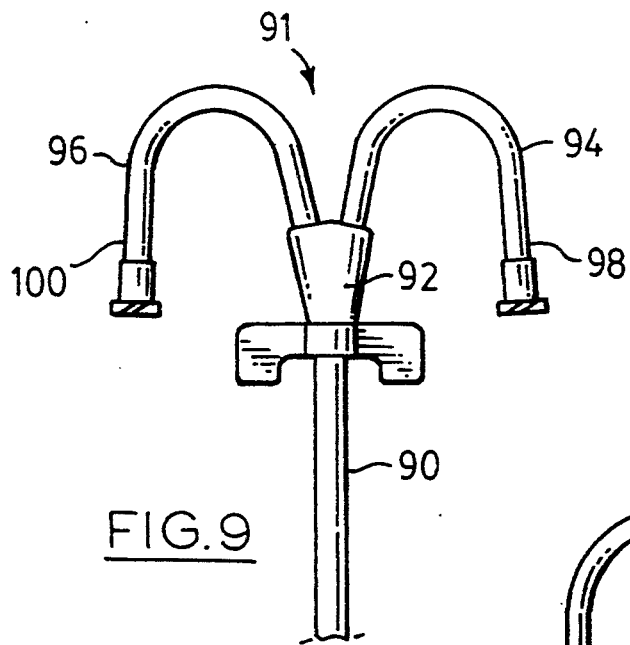
FIGS. 9 and 10 are diagrammatic views illustrating proximal ends of alternative embodiments of catheters.

Reference is next made to FIG. 9 which illustrates another embodiment of catheter incorporating the invention and especially useful for jugular access. A main body 90 has attachment structure 91 including a connector 92 (which is similar to connector 24 in FIG. 1) to respective intake and return tubes 94, 96 which are bent so that they include proximal portions 98, 100 which are generally parallel both with one another and with the longitudinal axis of the main body 90. This permits the catheter to be located in a dressing on the patient with the tubes 94, 96 connected to the dialysis equipment more conveniently and also permits the tubes to be stored in a dressing with a minimum of discomfort to the patient.

Figure 10:
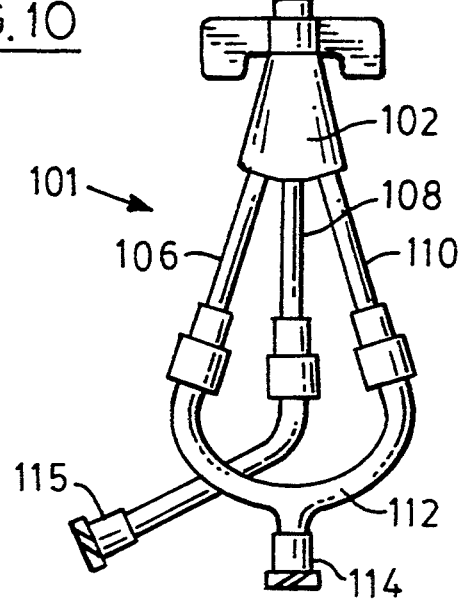

Another embodiment is shown in FIG. 10. In this embodiment an attachment structure 101 at the proximal end includes a connector 102 which is more conventional in that each of the three lumens in a main body 104 is connected to respective individual tubes 106, 108 and 110. The side lumens are connected externally of the connector 102 by coupling tubes 106 and 110 to a Y-fitting 112 which in turn leads to a single attachment device 114. The central lumen is led via tube 108 to a similar device 116. The arrangement permits the catheter to be used with all three tubes independently or coupled as shown.

FIG. 10 also shows another variation in that the main body is bent as is desirable in some uses. The cross-section of the catheter is particularly advantageous for creating and maintaining such curves. As previously mentioned the side lumens may end at blind walls equally spaced with respect to the distal end of the catheter. In FIG. 10, the side lumens end at transition 116 and side holes are provided adjacent the ends of these lumens.

These and other variations are within the scope of the invention as described and claimed.

I claim:

1. A dual flow catheter comprising:
  a main body extending longitudinally between proximal and distal ends and including a tip structure at the distal end, a transition portion extending from the tip structure, and a shaft extending from the transition portion to the proximal end, the main body containing parallel walls defining first and second side lumens extending from the proximal end to, the transition portion, and a central lumen defined between the parallel walls and positioned between the first and second side lumens the central lumen extending from the proximal to the distal end;
  attachment structure including first and second tubes extending generally longitudinally away from the main body at the proximal end, and a connector coupling the proximal end of the main body to the tubes with fluid communication between the first tube and both the first and second side lumens, and between the second tube and the central lumen whereby in use the first and second side lumens may be used simultaneously as intake lumens and the central lumen as a return lumen.

2. A dual flow catheter as claimed in claim 1 in which the side lumens have similar cross-sectional areas.

3. A dual flow catheter as claimed in claim 1 in which the sum of the cross-sectional areas of the side lumens is substantially equal to the cross-sectional area of the central lumen.

4. A dual flow catheter as claimed in claim 1 in which the first and second side lumens terminate at respective transverse openings.

5. A dual flow catheter as claimed in claim 1 in which the first and second lumens terminate at respective transverse openings extending outwardly at an angle no less than 30 degrees from the longitudinal direction measured towards the proximal end.

6. A dual flow catheter as claimed in claim 1 in which the central opening is shaped to receive a guide wire.

* * * * *